(12) United States Patent
Cerwin et al.

(10) Patent No.: US 8,383,030 B2
(45) Date of Patent: Feb. 26, 2013

(54) APPARATUS AND METHOD FOR MAKING SUTURE PACKAGES

(75) Inventors: Robert James Cerwin, Pipersville, PA (US); Clifford A. Dey, Riegelsville, PA (US)

(73) Assignee: Ethicon, Inc., Somerville, NJ (US)

(*) Notice: Subject to any disclaimer, the term of this patent is extended or adjusted under 35 U.S.C. 154(b) by 280 days.

(21) Appl. No.: 12/775,785

(22) Filed: May 7, 2010

(65) Prior Publication Data
US 2010/0276840 A1 Nov. 4, 2010

Related U.S. Application Data

(62) Division of application No. 11/495,303, filed on Jul. 28, 2006, now Pat. No. 7,837,455.

(51) Int. Cl.
*B29C 45/00* (2006.01)

(52) U.S. Cl. .................. 264/297.2; 264/328.7; 425/185; 249/102

(58) Field of Classification Search .................. 264/219, 264/328.1, 328.7; 425/185
See application file for complete search history.

(56) References Cited

U.S. PATENT DOCUMENTS

| | | | |
|---|---|---|---|
| 3,861,640 A | 1/1975 | Agneta |
| 4,861,254 A | 8/1989 | Takeuchi |
| 4,967,902 A | 11/1990 | Sobel et al. |
| 5,052,551 A | 10/1991 | Cerwin et al. |
| 5,056,658 A | 10/1991 | Sobel et al. |
| 5,131,533 A | 7/1992 | Alpen |
| 5,165,217 A | 11/1992 | Sobel et al. |
| 5,179,818 A | 1/1993 | Kalinski et al. |
| 5,180,053 A | 1/1993 | Cascio et al. |
| 5,213,210 A | 5/1993 | Cascio et al. |
| 5,230,424 A | 7/1993 | Alpern et al. |
| 5,236,083 A | 8/1993 | Sobel |
| 5,255,889 A | 10/1993 | Collette et al. |
| 5,284,240 A | 2/1994 | Alpern |
| 5,628,395 A | 5/1997 | Daniele et al. |
| 5,655,652 A | 8/1997 | Sobel |
| 5,660,024 A | 8/1997 | Ivanov et al. |

(Continued)

FOREIGN PATENT DOCUMENTS

| EP | 1433370 B1 | 4/2003 |
|---|---|---|
| EP | 1087808 B1 | 12/2003 |

(Continued)

OTHER PUBLICATIONS

International Preliminary Report on Patentability mailed on Feb. 3, 2009 in connection with PCT/US2007/016838.

(Continued)

*Primary Examiner* — James Sanders
(74) *Attorney, Agent, or Firm* — Greenberg Traurig

(57) ABSTRACT

Apparatus and method for making a plurality of different types of suture packages employ a mold with first and second opposing mold parts partially defining a mold cavity, at least one of the opposing mold parts has an opening therein communicating with the mold cavity. An insert is removeably inserted into the opening, to complete the mold cavity in a form suitable for molding a first type of suture package. An alternative insert is interchangeable with the first insert for completing the mold cavity in a form suitable for molding a second type of suture package. To make different suture packages, the mold is initially configured and used with one of the inserts to thereby make one type of suture package. The first insert is then replaced with the second, changing the mold cavity to form another type of suture package.

4 Claims, 5 Drawing Sheets

U.S. PATENT DOCUMENTS

| | | | |
|---|---|---|---|
| 5,664,404 A | 9/1997 | Ivanov et al. | |
| 5,675,961 A | 10/1997 | Cerwin et al. | |
| 5,788,062 A | 8/1998 | Cerwin et al. | |
| 6,047,815 A * | 4/2000 | Cerwin et al. | 206/63.3 |
| 6,098,796 A | 8/2000 | Januzeli | |
| 6,116,886 A * | 9/2000 | Tasaka | 425/183 |
| 6,135,272 A | 10/2000 | Sobel et al. | |
| 6,149,420 A * | 11/2000 | Kim et al. | 425/192 R |
| 6,743,202 B2 | 6/2004 | Hirschman et al. | |
| 6,782,940 B2 | 8/2004 | Billiet et al. | |
| 6,853,559 B2 | 2/2005 | Panella et al. | |
| 6,885,563 B2 | 4/2005 | Panella et al. | |
| 6,888,235 B2 | 5/2005 | Lopata et al. | |
| 6,936,917 B2 | 8/2005 | Lopata et al. | |
| 2001/0034506 A1 | 10/2001 | Hirschman | |
| 2003/0193791 A1 | 10/2003 | Panella et al. | |
| 2003/0194832 A1 | 10/2003 | Lopata et al. | |
| 2003/0197198 A1 | 10/2003 | Panella et al. | |
| 2003/0202330 A1 | 10/2003 | Lopata et al. | |
| 2004/0135504 A1 | 7/2004 | Tamaki et al. | |
| 2006/0038477 A1 | 2/2006 | Tamaki et al. | |
| 2008/0165762 A1 | 7/2008 | Gilfix et al. | |

FOREIGN PATENT DOCUMENTS

| | | |
|---|---|---|
| EP | 1369458 A1 | 12/2003 |
| EP | 1433831 A1 | 6/2004 |
| WO | 99/65548 | 12/1999 |
| WO | 03/028095 A2 | 4/2003 |
| WO | 03/028420 A1 | 4/2003 |
| WO | 03/034799 A1 | 4/2003 |
| WO | 03/037054 A1 | 5/2003 |
| WO | 03/072341 A2 | 9/2003 |
| WO | 03/072341 A3 | 9/2003 |
| WO | WO 2008/013905 A2 | 1/2008 |
| WO | WO 2008/013905 A3 | 1/2008 |

OTHER PUBLICATIONS

Written Opinion mailed on Jan. 28, 2009 in connection with PCT/US2007/016838.

Office Action mailed on Jul. 20, 2009 in connection with U.S. Appl. No. 11/495,303, filed Jul. 28, 2006.

* cited by examiner

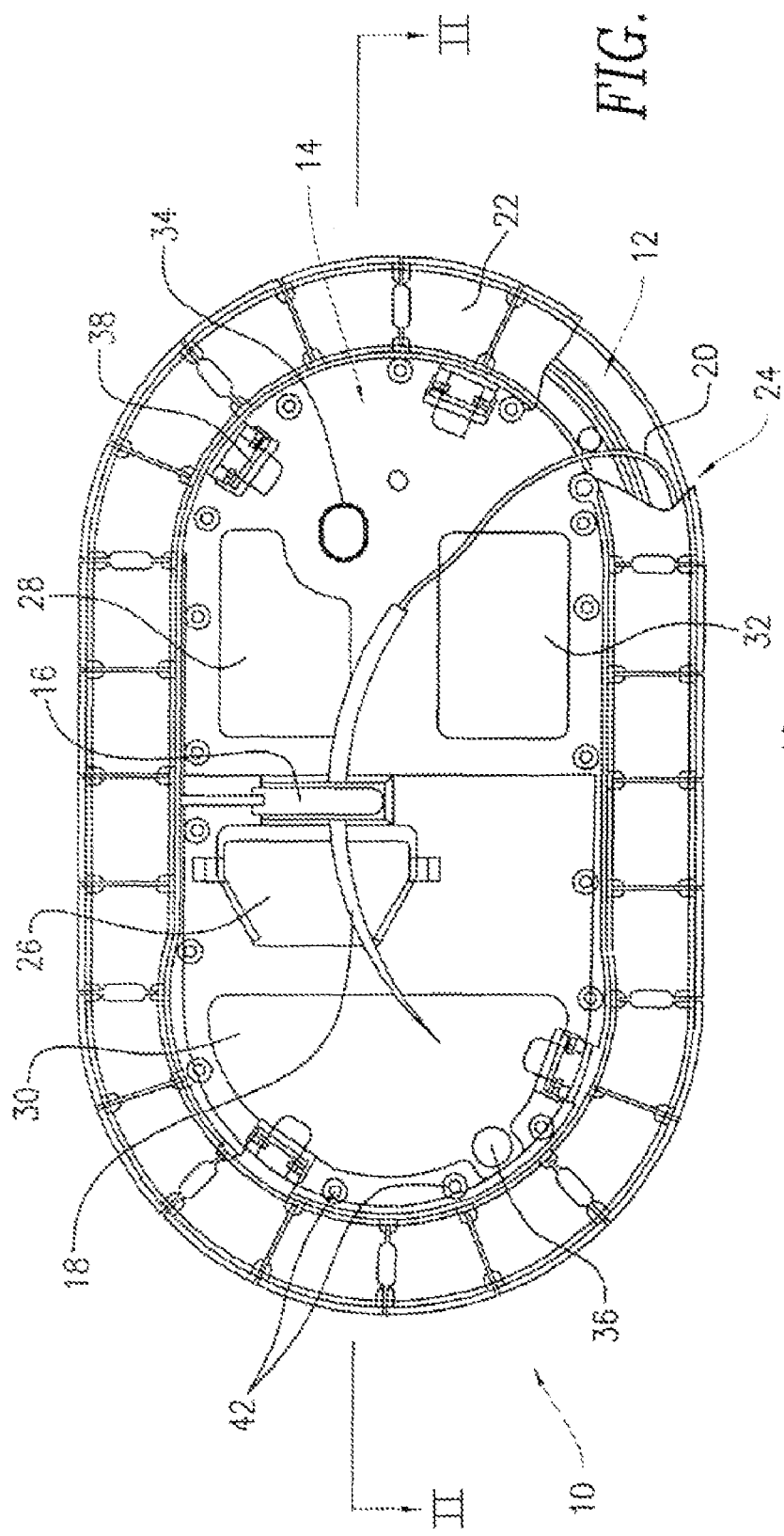
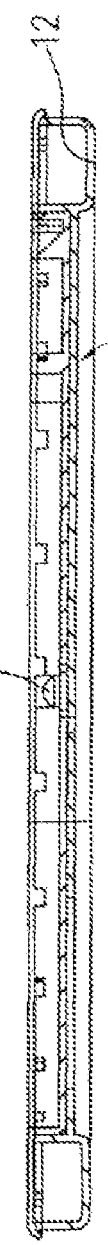
FIG. 1
FIG. 2

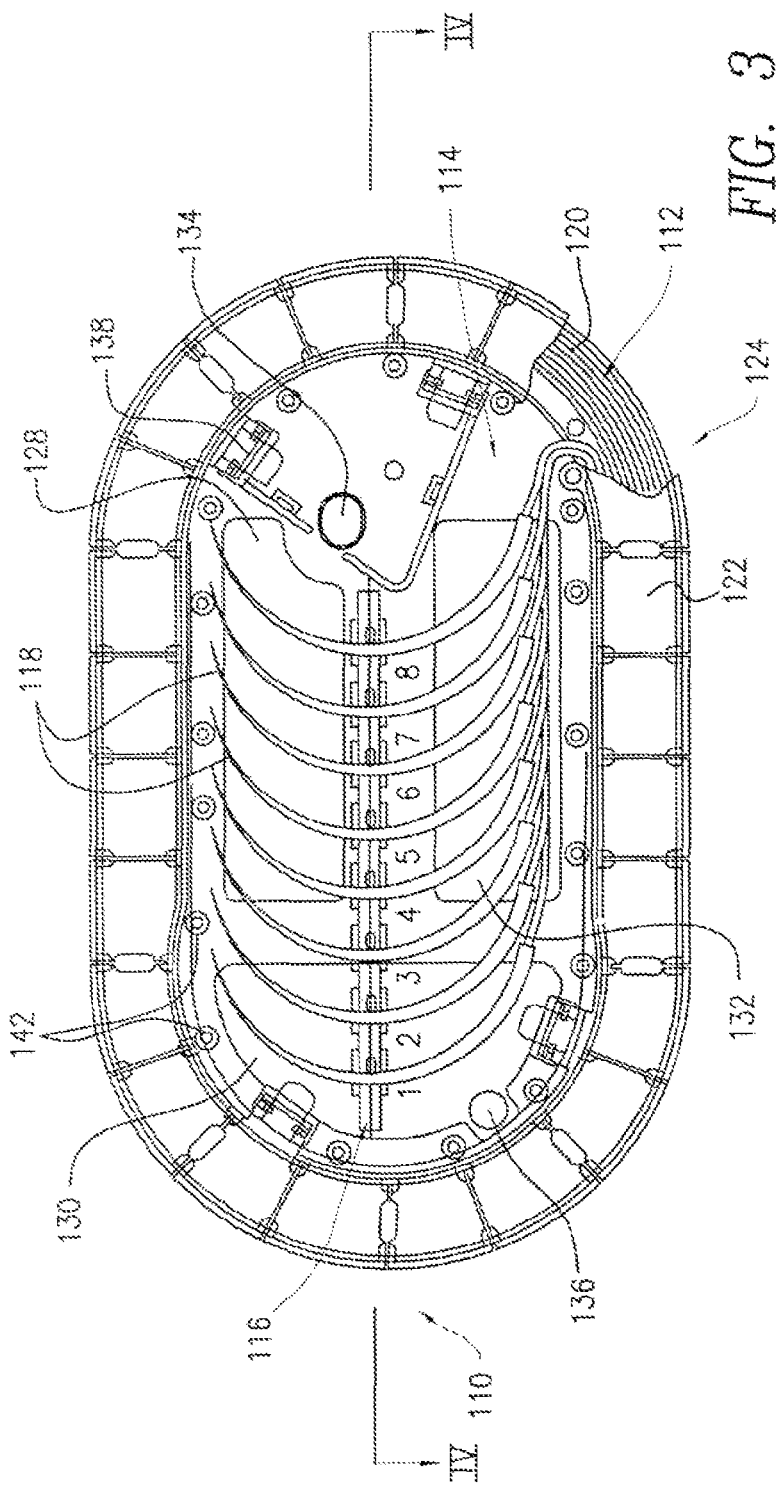
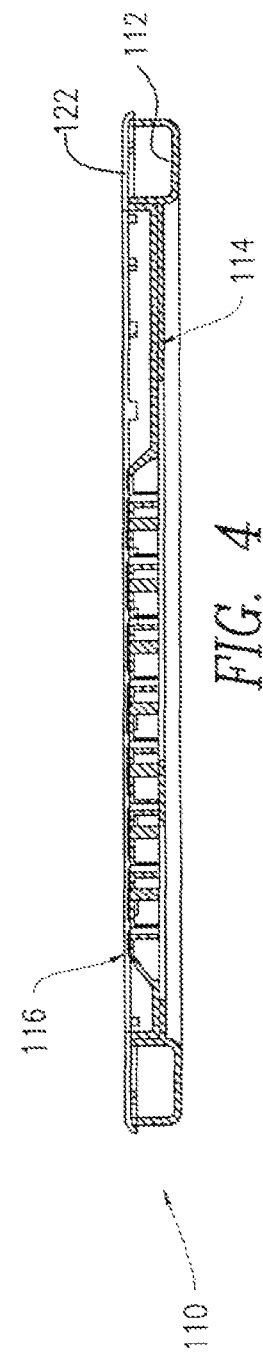
FIG. 3
FIG. 4

US 8,383,030 B2

APPARATUS AND METHOD FOR MAKING SUTURE PACKAGES

CROSS-REFERENCE TO RELATED APPLICATIONS

The present application is a divisional of U.S. patent application Ser. No. 11/495,303, filed on Jul. 28, 2006, now U.S. Pat. No. 7,837,455, the disclosure of which is incorporated by reference herein in its entirety.

FIELD OF THE INVENTION

The present invention relates to apparatus and methods for making suture packages and more particularly to suture packages utilizing a molded component made, e.g., by plastic injection molding.

BACKGROUND OF THE INVENTION

Various types of suture packages have been proposed to meet the needs of sterile and compact storage of armed and unarmed sutures, ease of handling while retrieving, opening and presentation of the suture (and needle if applicable) to the surgeon for effective and efficient dispensing from the package. In the operating room, small advances in the speed and reliability of procedures such as suture handling can confer a great benefit, in that surgical operations are time critical and allow no room for error or malfunction. One type of suture package that has proven beneficial has a generally oval, plastic "tray" with a peripheral "winding" or suture channel in which a wound coil of suture may be stored. An interior surface or "field" bounded by the suture channel serves as an area upon which one or a plurality of needles may be "parked", i.e., held by various means ("needle parks"). The tray may be covered by a paper or plastic lid, which may include a suture channel cover in the form of a plurality of cantilevered tabs extending over the suture channel when the cover is in place. A number of patents disclosing tray-type suture packages are owned by the assignee herein and are identified and incorporated by reference below.

There are a variety of sutures available for different surgical applications and these different sutures vary in suture/needle composition, gauge, needle shape, length, curvature, number, etc. and therefore require suture packages that are specifically designed to effectively hold and dispense them. Bach different type of suture package has, in the past, required the preparation of specific tooling, e.g., unique injection molding dies, which are expensive and time consuming to produce. It therefore remains an objective to facilitate and improve the efficiency of production of a variety of different suture packages.

SUMMARY OF THE INVENTION

The problems and disadvantages associated with conventional apparatus and techniques utilized to manufacture suture packages are overcome by the present invention, which includes a mold for making suture packages and having a first portion for forming a first surface of a first type of suture package, the first surface having a first shape. A second portion of the mold is suitable for forming a second surface of the first type of suture package, the second surface having a second shape. The second portion is removeably conjoinable to the first portion. An alternative second portion for forming an alternative second surface to that used in the first type of suture package is interchangeable with the second portion, yielding a second type of suture package with the alternative second surface having a third shape. The alternative second portion is removeably conjoinable to the first portion for producing the second type of suture package.

BRIEF DESCRIPTION OF THE DRAWINGS

The novel features of the present invention will be more readily apparent upon reading the following description in conjunction with the accompanying drawings, in which:

FIG. 1 is a plan view of a suture package made in accordance with a first embodiment of the present invention.

FIG. 2 is a cross-sectional view of the suture package of FIG. 1, taken along section line II-II and looking in the direction of the arrows.

FIG. 3 is a plan view of a suture package made in accordance with a second embodiment of the present invention.

FIG. 4 is a cross-sectional view of the suture package of FIG. 2, taken along section line IV-IV and looking in the direction of the arrows.

DETAILED DESCRIPTION OF THE INVENTION

Figure 5:
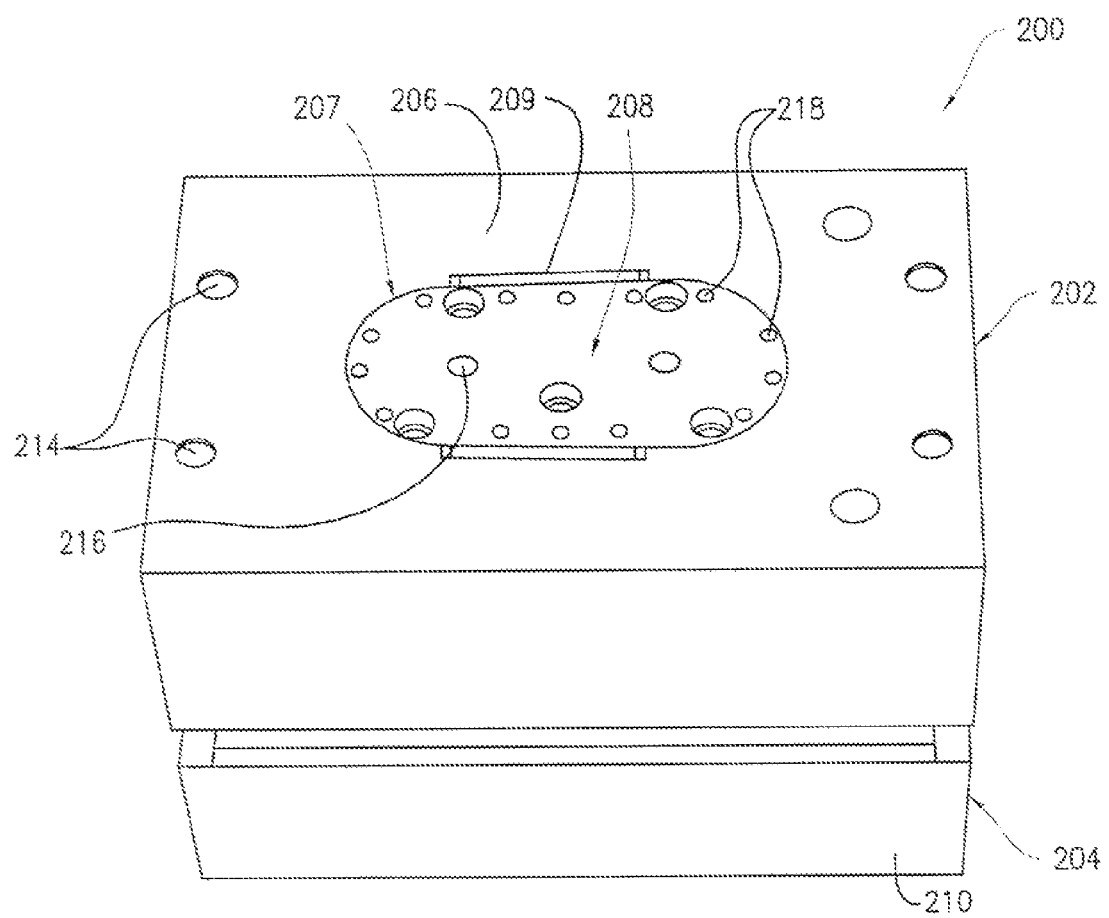
FIG. 5 is a perspective view of an assembled composite mold made in accordance with a third embodiment of the present invention.

The inventors of the present invention have recognized that the differences in suture packages for different types of suture needles frequently pertain to the area of the package within the winding channel, i.e., where the needle park is typically located, rather than the suture winding channel. FIGS. 1 and 2 show a first exemplary suture package 10 that may be made by the apparatus and methodology of the present invention. The suture package 10 has a peripheral suture channel 12 surrounding an interior field 14. The interior field 14 may be provided with a plurality of features, such as one or more needle parks 16 for holding needles 18 of an armed suture 20. The suture 20, which need not be armed with a needle 18, is wound into a coil and stored in the suture channel 12 under suture cover 22 with one end extending through a vent 24 in the suture cover 22. The interior field 14 may have a deflectable, hinged, needle access panel 26 and a plurality of areas having a reduced cross-sectional thickness 28, 30, 32, which are provided to minimize material usage. Apertures 34, 36 are provided to allow the suture package 10 to interact with machinery for loading the suture 20 into the package 10, such as for receiving locating dowels and winding pins (not shown), i.e., to allow a suture to be automatically wound in a suture winding machine and loaded into the suture package 10. Clips 38 retain a paper cover (not shown) over the interior field 14. A plurality of posts 42 and mating apertures (not shown) retain the suture cover 22 over the suture channel 12. The foregoing features are known in the art and are disclosed more fully in the following U.S. Pat. Nos. 6,135,272, 6,047,815, 5,230,424 and 5,179,818: each of which is incorporated herein for its teachings concerning various suture packages and their features. Suture packages of this type would typically be formed using plastic injection molding techniques.

FIGS. 3 and 4 show another exemplary suture package that can be made using the apparatus and methodology of the present invention. The reference numbers of FIGS. 3 and 4 relate to those of FIGS. 1 and 2, in that features and structures shown in FIGS. 3 and 4 having corresponding structure and/or functionality as those features depicted in FIGS. 1 and 2 are given the same reference numbers incremented by 100, unless described otherwise herein. One can readily appreciate that there are similarities and differences in the form and function of the suture package 110 shown in FIGS. 3 and 4 relative to the suture package 10 shown in FIGS. 1 and 2.

For example, the suture package 110 holds several needles 118 beside one another along the longitudinal axis of the suture package, whereas the suture package 10 has a single needle 18 parked on the interior field 14 and oriented generally along the longitudinal axis of the suture package 10. The suture package 10 has needle access panel 26, whereas the suture package 110 does not. There are numerous other distinctions between suture packages 10, 110. Notwithstanding the differences therebetween, there are also similarities between the suture packages 10, 110, e.g., the peripheral suture channels 12, 112 of each of the suture packages 10, 110 appear to be the same.

The inventors of the present invention have discovered that a variety of suture packages having common elements may be molded more efficiently and more economically by utilizing multi-part (composite) molds, wherein a portion of the mold that forms the common or constant portion of the suture package is used for producing each suture package of a series of different suture packages having this common portion. The common mold portion is conjoined with a variable mold portion which forms the portion of the suture package that is unique for each of the plurality of different packages in the series.

Figure 6:
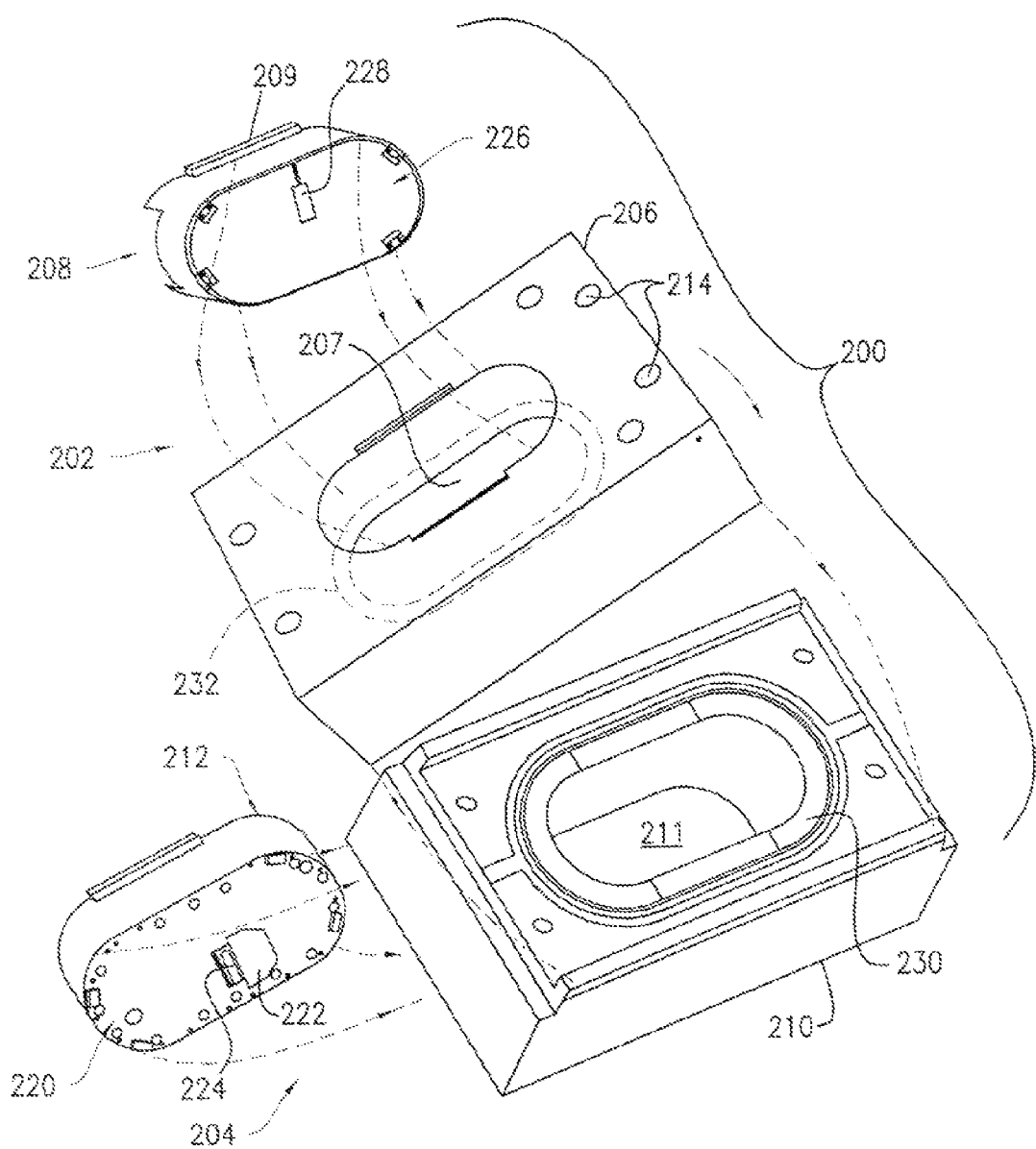
FIG. 6 is an exploded perspective view of the mold of FIG. 5.

FIGS. 5 and 6 show a composite mold 200 made in accordance with the present invention and having upper and lower subassemblies 202, 204. The upper subassembly 202 has an outer peripheral mold portion or "chase" 206 with an aperture 207 near the center thereof for receiving an inner mold portion or "insert" 208. The insert 208 has a pair of tabs 209 that control the depth that the insert 208 extends into the aperture 207. The lower subassembly 204 of the mold 200 has a similar layout, having an outer chase 210 with an internal aperture 211 that slideably receives a corresponding insert 212. The composite mold 200 therefore has four main parts 206, 208, 210 and 212. Fastener apertures 214 receive fasteners (not shown) extending therethrough to secure the upper and lower assemblies 202, 204 to opposed platens of an injection molding machine (not shown). When the upper and lower subassemblies 202, 204 are abutted together within the injection molding machine, they define an internal molding cavity for forming a suture package, e.g., 10, 110. After the injection of plastic into the molding cavity, the upper and lower subassemblies 202, 204 are separated to remove the molded product from the molding cavity. This is typically facilitated by conventional ejector pins (not shown). A plurality of ejector pin passageways 218 extend through the composite mold 200 to admit the ejector pins, which are extensible into the mold cavity to eject the molded package 10, 110 therefrom. Shutoff apertures 216 may be provided to admit a shutoff pin (not shown), e.g., for forming an aperture, e.g., 34, 134 in the suture packages 10, 110, respectively. The composite mold 200, when assembled, has a contiguous mold cavity defined by surfaces on the four mold parts 206, 208, 210 and 212 (and any shutoffs that may be employed). More particularly, the exterior bottom surface of the peripheral suture channel, e.g., 12 (see FIG. 1) is delimited in the mold cavity by surface 230 of lower chase 210; the top interior surface of the suture channel 12 is delimited by the surface 232 (shown in dotted lines) of upper chase 206; the bottom surface of the interior field 14 of suture package 10 is delimited by surface 220 of insert 212, including needle clip bottom surface 224 and access door bottom surface 222; and the top surface of the interior field 14 is delimited by surface 226 of insert 208, which includes a surface 228 for forming the top surface of the needle park 16.

Figure 7:
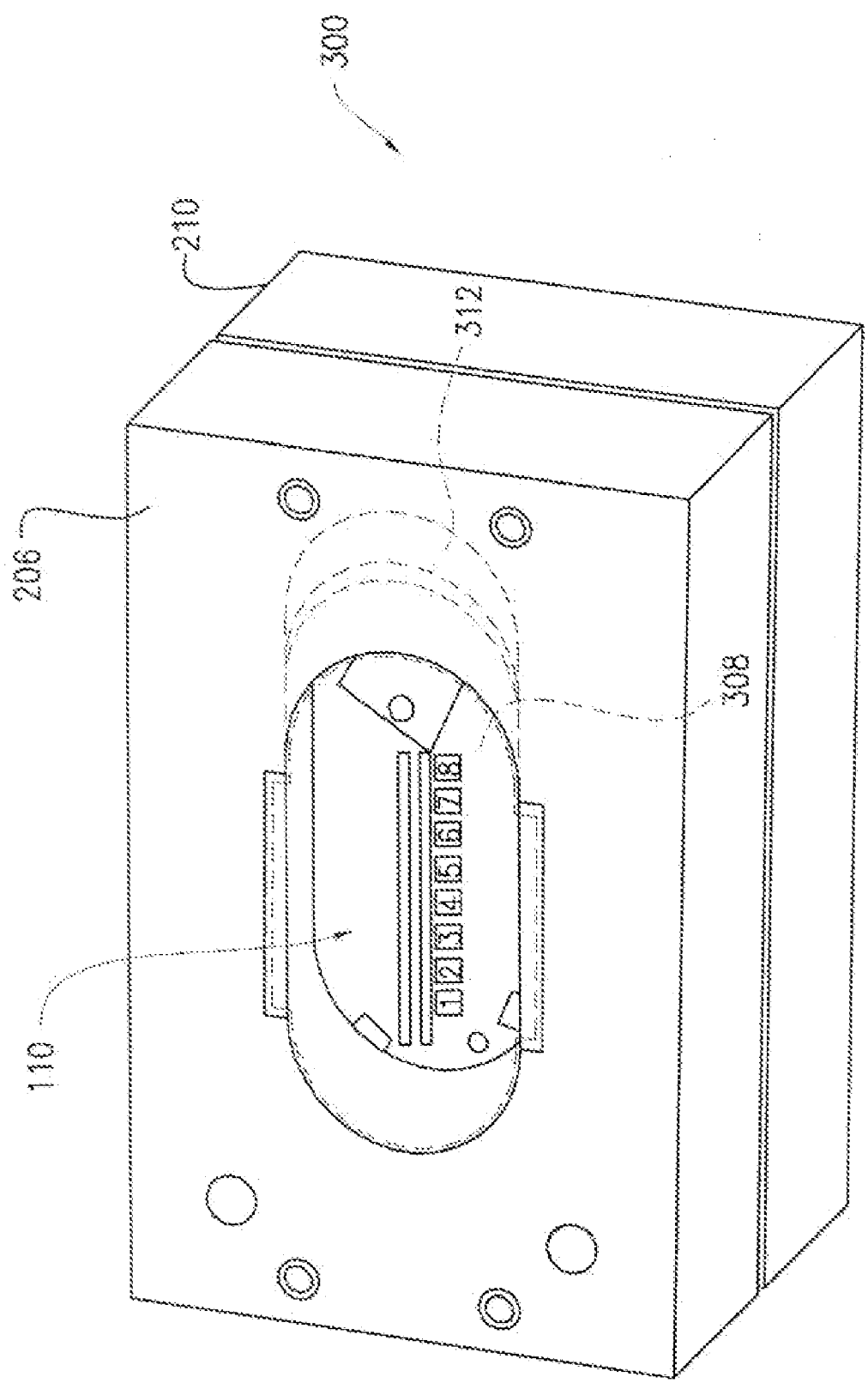
FIG. 7 is a perspective view of a partially dissembled composite mold made in accordance with a fourth embodiment of the present invention, showing a portion of a suture package therein.

FIG. 7 illustrates that a composite mold 300 for forming a suture package 110 may be formed by utilizing the same upper and lower chases 206, 210 as were used in the composite mold 200, but with different inserts 308, 312 (shown in phantom). Mold 300 will therefore produce a suture package 110, such as is shown in FIGS. 3 and 4. As a result, a portion of the suture packages 10, 110, e.g., the suture channel 12, 112, which remains the same for different suture packages in a series, may be formed by one or more portions of the composite mold which remain constantly in use for molding each suture package in the series of different suture packages. The portion of the suture packages in a series of different suture packages that changes for each different package, e.g., the interior field 14, 114, can be formed by one or more portions of the composite mold 200, 300 that are changed for the formation of each different type of package. The ability to retain common portions of the mold for producing different packages results in a simplification of mold making, representing a substantial savings in energy, materials, labor and time.

While the present invention has been explained in terms of the embodiments shown, various modifications could be made by those skilled in the art which would fall within the scope of this invention and which are intended to be covered by the appended claims. For example, while a four-part composite mold is shown, a mold having greater or fewer parts may be employed without departing from the spirit or scope of the present invention.

We claim:

1. A method for making a type of suture package having an interior field for receiving one or more needles and a suture channel at least partially surrounding the interior field, said method comprising the steps of:

providing first and second mold portions cooperating to define a mold cavity therebetween when the first and second mold portions are in an abutting relationship to each other, the first mold portion having a first internal mold surface on a side of the first mold portion facing the mold cavity and a first external mold surface on a side of the first mold portion opposite the first internal mold surface the first mold portion defining an opening surrounded thereby and extending from the first internal mold surface to the first external mold surface, the first internal mold surface being arranged to provide shape to the first side of the suture channel, the second mold portion having a second internal mold surface on a side of the second mold portion facing the mold cavity and a second external mold surface on a side of the second mold portion opposite the second internal mold surface, the second internal mold surface being arranged to provide shape to the second side of the suture channel;

providing a first insert having a first surface and a second surface opposite the first surface, the first insert arranged to be removably insertable into the opening defined by the first mold portion from outside of the mold cavity so as to close the opening defined by the first mold portion, and so that the first surface of the first insert completes the first internal mold surface and the second surface of the first insert completes the first external mold surface, the first surface of the first insert being arranged to provide shape to a first side of a first type of interior field;

providing an alternative first insert having an alternative first surface and an alternative second surface opposite the alternative first surface the alternative first insert arranged to be removably insertable into the opening interchangeably with the first insert from outside of the mold cavity so as to close the opening and so that the alternative first surface of the alternative first insert completes the first internal mold surface and the alternative second surface of the alternative first insert completes the first external mold surface, the alternative first surface of the alternative first insert being arranged to provide shape to the first side of a second type of interior field that has a different shape than the first type of the interior field;

placing the first and second mold portions in the abutting relationship to each other so that the first and second mold portions define the mold cavity;

inserting the first insert into the opening defined by the first mold portion from outside of the mold cavity so as to close the opening defined by the first mold portion and complete the first internal mold surface.

2. The method of claim 1, comprising the further steps of:

injecting a material suitable for forming suture packages into the mold cavity to form a suture package having the first type of interior field with the first side of the first type of interior field having a shape defined by the first surface of the first insert and the first side of the suture channel having a shape provided by the first internal mold surface;

separating the first and second mold portions so as to open the mold cavity;

removing the suture package from either the first mold portion or the second mold portion;

removing the first insert from the opening defined by the first mold portion;

placing the first and second mold portions in the abutting relationship to each other so that the first and second mold portions define the mold cavity;

inserting the alternative first insert into the opening defined by the first mold portion from outside of the mold cavity so as to close the opening defined by the first mold portion and complete the first internal mold surface; and injecting a material suitable for forming suture packages into the mold cavity to form a suture package having the second type of interior field with the first side of the second type of interior field having a shape defined by the first surface of the alternative first insert and the first side of the suture channel having a shape provided by the first internal mold surface.

3. The method of claim 1, wherein the interior field of the type of suture package has a second side opposite the first side of the interior field and the second mold portion defines an opening surrounded thereby and extending from the second internal mold surface to the second external mold surface; said method comprising the further steps of:

providing a second insert having a third surface and a fourth surface opposite the third surface, the second insert arranged to be removably insertable into the opening defined by the second mold portion from outside of the mold cavity so as to close the opening defined by the second mold portion, and so that the third surface of the second insert completes the second internal mold surface and the fourth surface of the second insert completes the second external mold surface, the third surface of the second insert being arranged to provide shape to the second side of a third type of interior field;

providing an alternative second insert having an alternative third surface and an alternative fourth surface opposing the alternative third surface, the alternative third surface arranged to be removably insertable into the opening defined by the second mold portion interchangeably with the second insert from outside of the mold cavity so as to close the opening defined by the second mold portion and so that the alternative third surface of the alternative second insert completes the second internal mold surface and the alternative fourth surface of the alternative second insert completes the second external mold surface, the alternative third surface of the alternative second insert being arranged to provide shape to a second side of a fourth type of interior field that has a different shape than the third type of interior field;

inserting the second insert into the opening defined by the second mold portion from outside of the mold cavity so as to close the opening defined by the second mold portion and complete the second internal mold surface; and injecting a material suitable for forming suture packages into the mold cavity to form a suture package having the third type of interior field with the second side of the third type of interior field having a shape defined by the third surface of the second insert and the second side of the suture channel having a shape provided by the second internal mold surface.

4. The method of claim 3, comprising the further steps of:

separating the first and second mold portions so as to open the mold cavity;

removing the suture package from either the first mold portion or the second mold portion;

removing the second insert from the opening defined by the second mold portion;

placing the first and second mold portions in the abutting relationship to each other so that the first and second mold portions define the mold cavity;

inserting the alternative second insert into the opening defined by the second mold portion from outside of the mold cavity so as to close the opening defined by the second mold portion and complete the second internal mold surface; and injecting a material suitable for forming suture packages into the mold cavity to form a suture package having the fourth type of interior field with the second side of the fourth type of interior field having a shape defined by the alternative fourth surface of the alternative second insert and the second side of the suture channel having a shape provided by the second internal mold surface.

* * * * *